United States Patent [19]
Zones et al.

[11] Patent Number: 5,846,400
[45] Date of Patent: Dec. 8, 1998

[54] METHODS OF USING ZEOLITE SSZ-42

[75] Inventors: Stacey I. Zones, San Francisco; Andrew Rainis, Walnut Creek, both of Calif.

[73] Assignee: Chevron U.S.A. Inc., San Francisco, Calif.

[21] Appl. No.: 835,885

[22] Filed: Apr. 8, 1997

Related U.S. Application Data

[62] Division of Ser. No. 574,559, Dec. 14, 1995, Pat. No. 5,653,956, which is a continuation of Ser. No. 199,040, Dec. 18, 1994, abandoned.

[51] Int. Cl.$^6$ .............................. C10G 47/02; C10G 35/06
[52] U.S. Cl. .............................. 208/46; 208/27; 208/108; 208/110; 208/113; 208/134; 208/141; 208/109; 208/120; 585/407; 585/739; 585/750; 585/461; 585/475; 585/671; 585/666; 585/481; 585/733; 585/640

[58] Field of Search .................... 208/120, 46, 27, 208/108, 110, 113, 134.41, 100; 585/407, 739, 750, 467, 475, 671, 666, 481, 733, 640

[56] References Cited

U.S. PATENT DOCUMENTS

| | | | |
|---|---|---|---|
| 5,653,956 | 8/1997 | Zones | 423/706 |
| 5,685,973 | 11/1997 | Zones et al. | 208/120 |

*Primary Examiner*—Helane Myers
*Attorney, Agent, or Firm*—Richard J. Sheridan

[57] ABSTRACT

The present invention relates to new crystalline zeolite SSZ-42 prepared by processes for preparing crystalline molecular sieves, particularly large pore zeolites, using an organic templating agent selected from the group consisting of N-benzyl-1,4-diazabicyclo[2.2.2]octane cations and N-benzyl-1-azabicyclo[2.2.2]octane cations.

26 Claims, 1 Drawing Sheet

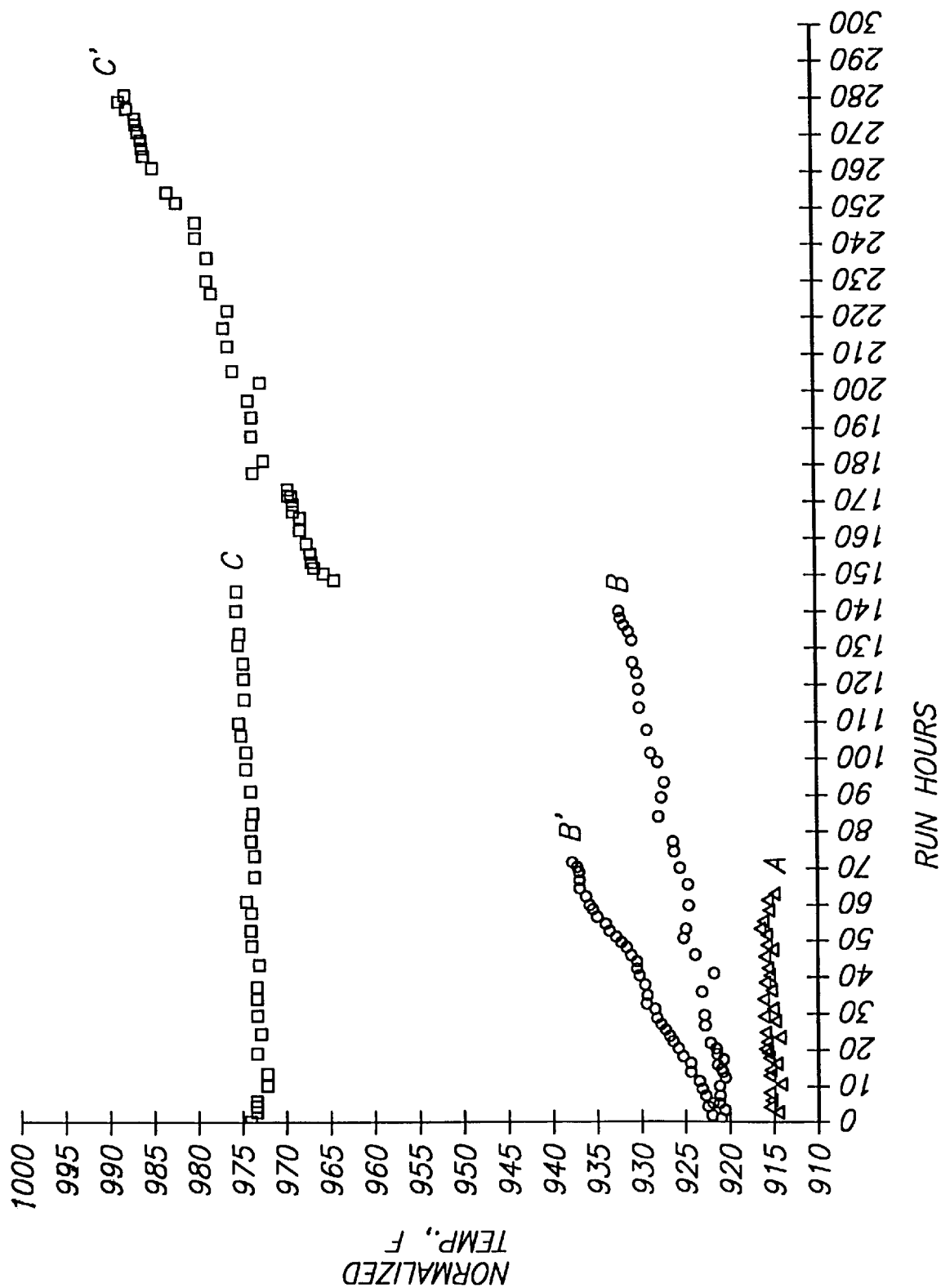

METHODS OF USING ZEOLITE SSZ-42

This application is a division of application Ser. No. 08/574,559, filed Dec. 14, 1995 now U.S. Pat. No. 5,653, 936, which is a continuation of application Ser. No. 08/199, 040, filed Feb. 18, 1994, now abandoned, both of which are incorporated by reference herein in their entirety.

BACKGROUND OF THE INVENTION

1. Field of the Invention

The present invention relates to new crystalline zeolite SSZ-42 prepared using an N-benzyl-1,4-diazabicyclo[2.2.2] octane cation or N-benzyl-1-azabicyclo[2.2.2]octane cation templating agent, and hydrocarbon conversion processes using SSZ-42 as a catalyst.

2. State of the Art

In conventional usage the term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process. The term "zeolite" refers to a molecular sieve containing a silicate lattice, usually in association with some aluminum, boron, gallium, iron, and/or titanium. In the following discussion and throughout this disclosure, the terms molecular sieve and zeolite will be used more or less interchangeably. One skilled in the art will recognize that the teachings relating to zeolites are also applicable to the more general class of materials called molecular sieves.

Natural and synthetic crystalline molecular sieves are useful as catalysts and adsorbents. Each crystalline molecular sieve is distinguished by a crystal structure with an ordered pore structure, and is characterized by a unique X-ray diffraction pattern. Thus, the crystal structure defines cavities and pores which are characteristic of the different species. The adsorptive and catalytic properties of each crystalline molecular sieve are determined in part by the dimensions of its pores and cavities. Accordingly, the utility of a particular molecular sieve in a particular application depends at least partly on its crystal structure.

Because of their unique sieving characteristics, as well as their catalytic properties, crystalline molecular sieves are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

Organic templating agents are believed to play an important role in the process of molecular sieve crystallization. Organic amines and quaternary ammonium cations were first used in the synthesis of zeolites in the early 1960s as reported by R. M. Barrer and P. J. Denny in *J. Chem. Soc.* 1961 at pages 971–982. This approach led to a significant increase in the number of new zeolitic structures discovered as well as an expansion in the boundaries of composition of the resultant crystalline products.

Previously, products with low silica to alumina ratios ($SiO_2/Al_2O_3 \leq 10$) had been obtained, but upon using the organocations as components in the starting gels, zeolites with increasingly high $SiO_2/Al_2O_3$ were realized. Some of these materials are summarized by R. M. Barrer 1982, *Hydrothermal Chemistry of Zeolites*, New York: Academic Press, Inc.

Unfortunately, the relationship between structure of the organocation and the resultant zeolite is far from predictable, as evidenced by the multitude of products which can be obtained using a single quaternary ammonium salt as reported by S. I. Zones et al., 1989, *Zeolites: Facts, Figures, Future*, ed. P. A. Jacobs and R. A. van Santen, pp. 299–309, Amsterdam: Elsevier Science Publishers, or the multitude of organocations which can produce a single zeolitic product as reported by R. M. Barrer, 1989, *Zeolite Synthesis*, ACS Symposium 398, ed. M. L. Occelli and H. E. Robson, pp. 11–27, American Chemical Society.

Thus, it is known that organocations exert influence on the zeolite crystallization process in many unpredictable ways. Aside from acting in a templating role, the organic cation's presence also greatly affects the characteristics of the gel. These effects can range from modifying the gel pH to altering the interactions of the various components via changes in hydration (and thus solubilities of reagents) and other physical properties of the gel. Accordingly, investigators have now begun to consider how the presence of a particular quaternary ammonium salt influences many of these gel characteristics in order to determine more rigorously how such salts exert their templating effects.

U.S. Pat. No. 5,194,235, issued Mar. 6, 1993 to Zones, discloses the use of a templating agent known as DABCO-$C_n$-diquat to prepare the zeolite SSZ-16. This templating agent has the following formula:

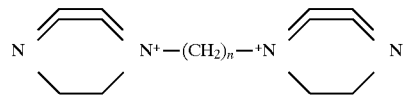

wherein n is 3, 4 or 5.

is In summary, a variety of templates have been used to synthesize a variety of molecular sieves, including zeolites of the silicate, aluminosilicate, and borosilicate families. However, the specific zeolite which may be obtained by using a given template is at present unpredictable. In fact, the likelihood of any given organocation serving as an effective template useful in the preparation of a molecular sieve is conjectural at best. In particular, organocation templating agents have been used to prepare many different combinations of oxides with molecular sieve properties, with silicates, aluminosilicates, aluminophosphates, borosilicates and silicoaluminophosphates being well known examples.

SUMMARY OF THE INVENTION

In accordance with the present invention there is provided a zeolite having a mole ratio of an oxide selected from silicon oxide, germanium oxide and mixtures thereof to an oxide selected from aluminum oxide, gallium oxide, iron oxide, titanium oxide, boron oxide and mixtures thereof greater than about 10 and having the X-ray diffraction lines of Table I.

The present invention also provides a zeolite having an average pore size diameter greater than about 6 Angstroms and having the X-ray diffraction lines of Table II.

In accordance with the present invention there is further provided a zeolite having a composition, as-synthesized and in the anhydrous state, in terms of mole ratios as follows:

| | |
|---|---|
| $YO_2/W_2O_3$ | Greater than or equal to 15 |
| $YO_2/M_2O$ | Greater than or equal to 45 |
| $YO_2/Q$ | 10–40 | wherein Q is comprised of cations selected from the group consisting of N-benzyl-1,4-diazabicyclo[2.2.2]octane cations and N-benzyl-1-azabicyclo[2.2.2]octane cations, M is an alkali metal cation or alkaline earth metal cation, W is a trivalent atom selected from the group consisting of boron, aluminum, gallium, iron, titanium, and mixtures thereof wherein at least 50% of W is boron, and Y is selected from the group consisting of silicon, germanium, and mixtures thereof and having the X-ray diffraction lines of Table I.

In accordance with this invention, there is also provided a zeolite prepared by thermally treating (calcining) a zeolite having a mole ratio of an oxide selected from silicon oxide, germanium oxide and mixtures thereof to an oxide selected from aluminum oxide, gallium oxide, iron oxide, titanium oxide, boron oxide and mixtures thereof greater than about 10 and having the X-ray diffraction lines of Table I at a temperature of from about 200° C. (392° F.) to about 800° C. (1472° F.), the thus-treated zeolite having the X-ray diffraction lines of Table II. The present invention also includes the hydrogen form of this thus-prepared zeolite, which hydrogen form is prepared by ion exchanging with an acid or with a solution of an ammonium salt followed by a second thermal treatment.

In accordance with the present invention there is also provided a catalyst comprising the aforesaid hydrogen form of the zeolite of this invention.

The present invention additionally provides a process for converting hydrocarbons comprising contacting a hydrocarbonaceous feed at hydrocarbon converting conditions with the catalyst of this invention.

Further provided by the present invention is a hydrocracking process comprising contacting a hydrocarbon feedstock under hydrocracking conditions with the catalyst of this invention.

This invention also includes a dewaxing process comprising contacting a hydrocarbon feedstock under dewaxing conditions with the catalyst of this invention.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. (104° F.) and less than about 300° C. (572° F.), under aromatic conversion conditions with the zeolite of this invention. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the aforementioned hydrogen form of the zeolite of this invention.

Also included in this invention is such a catalytic cracking process wherein the catalyst additionally comprises a large pore crystalline cracking component.

The present invention further provides an isomerizing process for isomerizing $C_4$ to $C_7$ hydrocarbons, comprising contacting a catalyst, comprising at least one Group VIII metal and the hydrogen form catalyst of this invention, with a feed having normal and slightly branched $C_4$ to $C_7$ hydrocarbons under isomerizing conditions.

Also provided is such an isomerization process wherein the catalyst has been calcined in a steam/air mixture at an elevated temperature after impregnation of the Group VIII metal, preferably platinum.

This invention also provides a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the hydrogen form catalyst of this invention.

This invention additionally provides a process for transalkylating an aromatic hydrocarbon which comprises contacting under transalkylating conditions an aromatic hydrocarbon with a polyalkyl aromatic hydrocarbon under at least partial liquid phase conditions and in the presence of the hydrogen form catalyst of this invention.

Further provided by this invention is a process to convert paraffins to aromatics which comprises contacting paraffins with the hydrogen form catalyst of this invention, said catalyst comprising gallium, zinc, lead or indium or a compound of gallium, zinc, lead or indium.

This invention also provides a process for converting lower alcohols and other oxygenated hydrocarbons comprising contacting said lower alcohol or other oxygenated hydrocarbon with the hydrogen form catalyst of this invention under conditions to produce liquid products.

This invention also provides a process for isomerizing olefins comprising contacting said olefin with the catalyst of this invention in its hydrogen form under conditions which cause isomerization of the olefin. One example of such a process is the isomerization of n-butene to isobutene.

The full scope of the present invention will be apparent to those familiar with molecular sieve synthesis from the following detailed description of the principle features of SSZ-42 and from the examples which accompany the description.

BRIEF DESCRIPTION OF THE DRAWING

The drawing is a graph showing run hours versus temperature for a reforming reaction using the catalyst of this invention (plot A), a commercially available catalyst (plots B and B') and a platinum-containing cesium beta zeolite catalyst (plots C and C').

DETAILED DESCRIPTION OF THE INVENTION

Principle Features

The present invention comprises a family of crystalline multidimensional large pore zeolites, SSZ-42. As used herein the term "large pore" means having an average pore size diameter greater than about 6 Angstroms, preferably from about 6.5 Angstroms to about 7.5 Angstroms.

SSZ-42 zeolites can be prepared from an aqueous solution comprising sources of an alkali or alkaline earth metal oxide, the templating agent, and sources of the desired trivalent element oxides and tetravalent element oxides. The reaction mixture should have a composition, in terms of mole ratios, within the ranges shown in Table A.

TABLE A

SSZ-42 REACTION MIXTURE

| | Broad | Preferred |
|---|---|---|
| $YO_2/W_2O_3$ | 5 and greater (to about 100) | 15 and greater (to about 100) |
| $OH-/YO_2$ | 0.05 to 0.50 | 0.15 to 0.30 |
| $Q/YO_2$ | 0.10 to 1.0 | 0.10 to 0.25 |
| $M+/YO_2$ | 0.01 to 0.50 | 0.03 to 0.10 |
| $H_2O/YO_2$ | 15 to 100 | 20 to 50 |
| $Q/Q+M^+$ | 0.50 to 0.95 | 0.66 to 0.90 | wherein Q is comprised of cations selected from the group consisting of N-benzyl-1,4-diazabicyclo[2.2.2]octane cations and N-benzyl-1-azabicyclo[2.2.2]octane cations, M is an alkali metal cation or alkaline earth metal cation, W is selected from the group aluminum, gallium, iron, boron, titanium and mixtures thereof wherein at least 50% of W is boron, and Y is selected from the group consisting of silicon, germanium, and mixtures thereof.

SSZ-42 can be made essentially aluminum free, i.e., having a silica to alumina mole ratio of ∞. The term "essentially alumina-free" is used because it is difficult to prepare completely aluminum-free reaction mixtures for synthesizing these materials. Especially when commercial silica sources are used, aluminum is almost always present to a greater or lesser degree. The hydrothermal reaction mixtures from which the essentially alumina-free crystalline siliceous molecular sieves may be prepared can be referred to as being substantially alumina free. By this usage is meant that no aluminum is intentionally added to the reaction mixture, e.g., as an alumina or aluminate reagent, and that to the extent aluminum is present, it occurs only as a contaminant in the reagents. An additional method of increasing the mole ratio of silica to alumina is by using standard acid leaching or chelating treatments. However, essentially aluminum-free SSZ-42 can be synthesized directly using essentially aluminum-free silicon sources as the only tetrahedral metal oxide component. SSZ-42 can also be prepared directly as a borosilicate, or as an alumino(boro)silicate by first preparing SSZ-42 as a borosilicate and then substituting aluminum for at least a portion of the boron by post synthesis treatment of the borosilicate.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued Dec. 17, 1985 to Chang et al., which is incorporated by reference herein in its entirety.

SSZ-42 as-synthesized has a mole ratio of tetravalent element oxides selected from silicon oxide, germanium oxide, and mixtures thereof to trivalent element oxides selected from aluminum oxide, gallium oxide, iron oxide, boron oxide, titanium oxide and mixtures thereof greater than about 10 wherein at least 50% of the trivalent element oxide is boron oxide; and has the X-ray diffraction lines of Table I below. SSZ-42 further has a composition, as-synthesized and in the anhydrous state, in terms of mole ratios indicated in Table B below.

TABLE B

AS-SYNTHESIZED SSZ-42

| | |
|---|---|
| $YO_2/W_2O_3$ | Greater than or equal to 15 |
| $YO_2/M_2O$ | Greater than or equal to 45 |
| $YO_2/Q$ | 10–40 | wherein Q, Y, W and M are as defined above, and wherein at least 50% of W is boron.

It is believed that SSZ-42 is comprised of a new framework structure or topology which is characterized by its X-ray diffraction pattern. SSZ-42 zeolites, as-synthesized, have a crystalline structure whose X-ray powder diffraction pattern exhibit the characteristic lines shown in Table I and is thereby distinguished from other known zeolites.

TABLE I

AS-SYNTHESIZED SSZ-42

| 2Theta | d/n | 100 I/I$_o$ |
|---|---|---|
| 8.26 | 10.70 | 70 |
| 9.76 | 9.05 | 7 |
| 16.54 | 5.355 | 15 |
| 19.16 | 4.628 | 21 |
| 20.64 | 4.300 | 100 |
| 21.58 | 4.115 | 23 |
| 21.80 | 4.074 | 49 |
| 23.72 | 3.748 | 10 |
| 23.92 | 3.717 | 35 |
| 24.96 | 3.565 | 11 |
| 25.38 | 3.506 | 12 |
| 26.24 | 3.393 | 26 |
| 26.78 | 3.326 | 26 |
| 29.46 | 3.030 | 18 |

The variation in the scattering angle (two theta) measurements, due to instrument error and to differences between individual samples, is estimated at ±0.20 degrees.

The X-ray diffraction pattern of Table I is representative of as-synthesized SSZ-42 zeolites. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

After calcination, the SSZ-42 zeolites have a crystalline structure whose X-ray powder diffraction pattern include the characteristic lines shown in Table II:

TABLE II

CALCINED SSZ-42

| 2Theta | d/n | 100 I/I$_o$ |
|---|---|---|
| 8.22 | 10.75 | 100 |
| 9.76 | 9.06 | 13 |
| 16.42 | 5.394 | 3 |
| 19.22 | 4.615 | 7 |
| 20.48 | 4.333 | 30 |
| 20.84 | 4.259 | 25 |
| 21.48 | 4.134 | 7 |
| 21.72 | 4.088 | 16 |
| 23.68 | 3.754 | 6 |
| 24.06 | 3.696 | 15 |
| 24.94 | 3.568 | 10 |
| 25.40 | 3.504 | 6 |
| 26.60 | 3.348 | 20 |
| 29.56 | 3.019 | 10 |

The variation in the scattering angle (two theta) measurements, due to instrument error and to indifferences between individual samples, is estimated at ±0.20 degrees.

Representative peaks from the X-ray diffraction pattern of calcined SSZ-42 are shown in Table II. Calcination can also result in changes in the intensities of the peaks as compared to patterns of the "as-synthesized" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

The X-ray powder diffraction patterns were determined by standard techniques. The radiation was the K-alpha/doublet of copper. A scintillation counter spectrometer with a strip-chart pen recorder was used. The peak heights I and the positions, as a function of 2θ where θ is the Bragg angle, were read from the relative intensities, $I/I_o$ where $I_o$ is the intensity of the strongest line or peak, and d, the interplanar spacing in Angstroms corresponding to the recorded lines, can be calculated.

The Preparation of SSZ-42 Zeolites

In preparing SSZ-42 zeolites, an N-benzyl-1,4-diazabicyclo[2.2.2]octane cation or N-benzyl-1-aza-bicyclo[2.2.2]octane cation may be used as a crystallization template in a manner known in the molecular sieve art. Thus, in general, SSZ-42 is prepared by contacting an active source of one or more oxides selected from the group consisting of monovalent element oxides, divalent element oxides, trivalent element oxides, and tetravalent element oxides with an organocation templating agent.

In practice, SSZ-42 is prepared by a process comprising:
(a) preparing an aqueous solution containing sources of the oxides listed in Table A above and at least one N-benzyl-1,4-diazabicyclo[2.2.2]octane cation or N-benzyl-1-azabicyclo[2.2.2]octane cation templating agent having an anionic counterion which is not detrimental to the formation of SSZ-42;
(b) maintaining the aqueous solution under conditions sufficient to form crystals of SSZ-42; and
(c) recovering the crystals of SSZ-42.

The N-benzyl-1,4-diazabicyclo[2.2.2]octane cation and N-benzyl-1-azabicyclo[2.2.2]octane cation templating agents which have been found to produce SSZ-42 have the following general formulas:

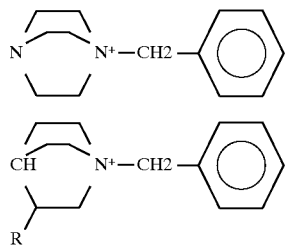

where R is —H, —OH or —$NH_2$.

Examples of the N-benzyl-1,4-diazabicyclo[2.2.2]octane cation templating agents useful in this invention include, but are not limited to, N-benzyl-1,4-diazabicyclo[2.2.2]octane cation, and examples of the N-benzyl-1-azabicyclo[2.2.2] octane cation templating agents useful in this invention include, but are not limited to, N-benzyl-1-azabicyclo[2.2.2] octane cation and N-benzyl-3-hydroxy-1-azabicyclo[2.2.2] octane cation.

SSZ-42 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides selected from the group consisting of one or more trivalent element (s), and one or more tetravalent element(s). The trivalent element is preferably selected from the group consisting of aluminum, boron, gallium, iron, titanium with at least 50% of the trivalent element being boron. Once the as-synthesized SSZ-42 material has been made, some or all of the boron may be replaced with, e.g., aluminum. Thus, in the calcined version of SSZ-42, the trivalent element is preferably aluminum, boron or combinations thereof. The tetravalent element is preferably selected from the group consisting of silicon, germanium, and combinations thereof. More preferably, the tetravalent element is silicon.

Typical sources of silicon oxide include silicates, silica hydrogel, silicic acid, fumed silica, colloidal silica, tetraalkyl orthosilicates, and silica hydroxides. Boron, as well as gallium, germanium, titanium, and iron can be added in forms corresponding to their silicon counterparts, i.e, as borates, boric acid and the like.

Typical sources of aluminum oxide for the reaction mixture include aluminates, alumina and aluminum compounds such as $AlCl_3$, $Al(SO_4)_3$, hydrated $Al(OH)_3$ gels, kaolin clays, colloidal aluminas, and the like.

Alternatively, a zeolite reagent may provide a source of aluminum or boron. In some cases, the source zeolite may provide a source of silica. In that case, the source zeolite in its dealuminated or deboronated form may be used as a source of silica, with additional silicon added using, for example, the conventional sources listed above. Use of a source zeolite reagent as a source of alumina for the present process is described in U.S. Pat. No. 4,503,024 issued on Mar. 5, 1985 to Bourgogne, et al. entitled "PROCESS FOR THE PREPARATION OF SYNTHETIC ZEOLITES, AND ZEOLITES OBTAINED BY SAID PROCESS", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, a hydroxide anion for a halide ion in the templating agent, thereby reducing or eliminating the alkali or alkaline earth metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-42 zeolite are formed. This hydrothermal crystallization is usually conducted under autogenous pressure, at a temperature between 100° C. (212° F.) and 200° C. (392° F.), preferably between 135° (275° F.) and 180° C. (356° F.). The crystallization period is typically greater than 1 day and preferably from about 3 days to about 7 days. The zeolite can be prepared with or without mild stirring or agitation.

During the hydrothermal crystallization step, the SSZ-42 crystals can be allowed to nucleate spontaneously from the reaction mixture. However, the use of SSZ-42 crystals as seed material can be advantageous in decreasing the time necessary for complete crystallization to occur. In addition, seeding can lead to an increased purity of the product obtained by promoting the nucleation and/or formation of SSZ-42 over any undesired phases. When used as seeds, SSZ-42 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. (194° F.) to 150° C. (302° F.) for from 8 to 24 hours, to obtain the as-synthesized, SSZ-42 zeolite crystals. The drying step can be performed at atmospheric pressure or under vacuum.

Crystalline SSZ-42 can be used as-synthesized or can be thermally treated (calcined). Usually, it is desirable to remove the alkali or alkaline earth metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via ion exchange techniques. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-42. The zeolite can also be impregnated with the metals, or the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank, et al.; 3,140,251 issued on Jul. 7, 1964 to Plank, et al.; and 3,140,253 issued on Jul. 7, 1964 to Plank, et al., each of which is incorporated by reference herein.

Following contact with the salt solution of the desired replacing cation, the zeolite is typically washed with water and dried at temperatures ranging from 65° C. (149° F.) to about 200° C. (392° F.). After washing, the zeolite can be calcined in air or inert gas at temperatures ranging from about 200° C. (392° F.) to about 800° C. (1472° F.) for periods of time ranging from 1 to 48 hours, or more, to produce a catalytically active product especially useful in hydrocarbon conversion processes.

Regardless of the cations present in the synthesized form of SSZ-42, the spatial arrangement of the atoms which form the basic crystal lattice of the zeolite remains essentially unchanged. The exchange of cations has little, if any effect on the zeolite lattice structure.

SSZ-42 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or, dried or partially dried and then extruded.

SSZ-42 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and copending U.S. patent application Ser. No. 959,205 now U.S. Pat. No. 5,316,753, filed Oct. 9, 1992 entitled "ZEOLITE SSZ-35", both of which are incorporated by reference herein in their entirety.

Hydrocarbon Conversion Processes

SSZ-42 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-42 are expected to be useful include catalytic cracking, hydrocracking, dewaxing, alkylation, and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., m-xylene), and disproportionating aromatics (e.g., toluene) to provide mixtures of benzene, xylenes and higher methylbenzenes and oxidation reactions. The SSZ-42 catalysts have high selectivity, and under hydrocarbon conversion conditions can provide a high percentage of desired products relative to total products.

SSZ-42 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

SSZ-42 can be used in hydrocarbon conversion reactions with active or inactive supports, with organic or inorganic binders, and with and without added metals. These reactions are well known to the art, as are the reaction conditions.

Hydrocracking

Using SSZ-42 catalyst which contains a hydrogenation promoter, heavy petroleum residual feedstocks, cyclic stocks and other hydrockate charge stocks can be hydrocracked using the process conditions and catalyst components disclosed in the aforementioned U.S. Pat. No. 4,910,006 and U.S. patent application Ser. No. 959,205now U.S. Pat. No. 5,316,753. Typically, these feedstocks can be hydrocracked at hydrocracking conditions including a temperature in the range of from 175° C. (347° F.) to 485° C. (905° F.), molar ratios of hydrogen to hydrocarbon charge from 1 to 100, a pressure in the range of from 0.5 to 350 bar, and a liquid hourly space velocity (LHSV) in the range of from 0.1 to 30.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation catalyst is present in an effective amount to provide the hydrogenation function of the hydrocracking catalyst, and preferably in the range of from 0.05 to 25% by weight.

Dewaxing

SSZ-42 can be used to dewax hydrocarbonaceous feeds by selectively removing straight chain paraffins. The catalytic dewaxing conditions are dependent in large measure on the feed used and upon the desired pour point. Generally, the temperature will be between about 200° C. (392° F.) and about 475° C. (887° F.), preferably between about 250° C. (482° F.) and about 450° C. (842° F.). The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling about 177° C. (350° F.).

The SSZ-42 hydrodewaxing catalyst may optionally contain a hydrogenation component of the type commonly employed in dewaxing catalysts. See the aforementioned U.S. Pat. No. 4,910,006 and U.S. patent application Ser. No. 959,205 for examples of these hydrogenation components. The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

Aromatics Formation

SSZ-42 can be used to convert light straight run naphthas and similar mixtures to highly aromatic mixtures. Thus, normal and slightly branched chained hydrocarbons, preferably having a boiling range above about 40° C. (104° F.) and less than about 300° C. (572° F.), can be converted to products having a substantial higher octane aromatics content by contacting the hydrocarbon feed with the zeolite at a temperature in the range of from about 400° C. (752° F.) to 600°C. (1112° F.), preferably 480° C. (896° F.) to 550° C. (1022° F.) at pressures ranging from atmospheric to 10 bar, and liquid hourly space velocities (LHSV) ranging from 0.1 to 15.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. patent application Ser. No. 959,205, now U.S. Pat. No. 5,316,753 for a description of such methods.

The preferred alkali metals are sodium, potassium, and cesium. The zeolite itself can be substantially free of acidity only at very high silica:alumina mole ratios; by "zeolite consisting essentially of silica" is meant a zeolite which is substantially free of acidity without base neutralization.

Catalytic Cracking

Hydrocarbon cracking stocks can be catalytically cracked in the absence of hydrogen using SSZ-42 at liquid hourly space velocities from 0.5 to 50, temperatures from about 127° C. (260° F.) to 885° C. (1625° F.) and pressures from subatmospheric to several hundred atmospheres, typically from about atmospheric to about 5 atmospheres.

For this purpose, the SSZ-42 catalyst can be composited with mixtures of inorganic oxide supports as well as a traditional large pore crystalline cracking catalyst.

As in the case of hydrocracking catalysts, when SSZ-42 is used as a catalytic cracking catalyst in the absence of hydrogen, the catalyst may be employed in conjunction with traditional cracking catalysts, e.g., any aluminosilicate heretofore employed as a component in cracking catalysts. Examples of these traditional cracking catalysts are disclosed in the aforementioned U.S. Pat. No. 4,910,006 and U.S. patent application Ser. No. 959,205, now U.S. Pat. No. 5,316,753. When a traditional cracking catalyst (TC) component is employed, the relative weight ratio of the TC to the SSZ-42 is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component. See the aforementioned U.S. Pat. No. 4,910,006 and U.S. patent application Ser. No. 959,205, now U.S. Pat. No. 5,316,753 for examples of such matrix components.

Oligomerization

It is expected that SSZ-42 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with SSZ-42 at a temperature of from about 232° C. (450° F.) to about 649° C. (1200° F.), a LHSV of from about 0.2 to about 50 and a hydrocarbon partial pressure of from about 0.1 to about 50 atmospheres.

Also, temperatures below about 232° C. (450° F.) may be used to oligomerize the feedstock, when the feedstock is in the liquid phase when contacting the zeolite catalyst. Thus, when the olefin feedstock contacts the zeolite catalyst in the liquid phase, temperatures of from about 10° C. (50° F.) to about 232° C. (450° F.), and preferably from 27° C. (80° F.) to 204° C. (400° F.) may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens, et al. which is incorporated totally herein by reference. If required, such zeolites may be obtained by steaming, by use in a conversion process or by any other method which may occur to one skilled in this art.

SSZ-42 can be used to convert light gas $C_2$–$C_6$ paraffins and/or olefins to higher molecular weight hydrocarbons including aromatic compounds. Operating temperatures of 100° C. (212° F.) to 700° C. (1292° F.), operating pressures of 0 to 1000 psig and space velocities of 0.5–40 hr$^{-1}$ WHSV (weight hourly space velocity) can be used to convert the $C_2$–$C_6$ paraffin and/or olefins to aromatic compounds. Preferably, the zeolite will contain a catalyst metal or metal oxide wherein said metal is selected from the group consisting of Groups IB, IIB, VIII and IIIA of the Periodic Table, and most preferably gallium or zinc and in the range of from about 0.05% to 5% by weight.

Condensation of Alcohols

SSZ-42 can be used to condense lower aliphatic alcohols having 1 to 10 carbon atoms to a gasoline boiling point hydrocarbon product comprising mixed aliphatic and aromatic hydrocarbon. The condensation reaction proceeds at a temperature of about 260° C. (500° F.) to 538° C. (1000° F.), a pressure of about 0.5 psig to 1000 psig and a space velocity of about 0.5 to 50 WHSV. The process disclosed in U.S. Pat. No. 3,894,107 issued Jul. 8, 1975 to Butter et al., describes the process conditions used in this process, which patent is incorporated totally herein by reference.

The catalyst may be in the hydrogen form or may be base is exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst with a hydrocarbon feed under isomerization conditions. The feed is preferably a light straight run fraction, boiling within the range of −1.1° C. (30° F.) to 121° C. (250° F.) and preferably from 16° C. (60° F.) to 93° C. (200° F.). Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50 psig and 1000 psig, more preferably between 100 psig and 500 psig. The liquid hourly space velocity (LHSV) is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. The temperature is preferably between about 93° C. (200° F.) and about 538° C. (1000° F.), more preferably between 204° C. (400° F.) and 316° C. (600° F.). See the aforementioned U.S. Pat. No. 4,910,006 and U.S. patent application Ser. No. 959,205, now U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. patent application Ser. No. 959,205, now U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S.

Pat. No. 4,910,006 and U.S. patent application Ser. No. 959,205, now U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

The isomerization catalyst may also be calcined in a steam/air mixture at an elevated temperature after impregnation with the Group VIII metal, preferably platinum.

Alkylation and Transalkylation

SSZ-42 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial C8 liquid phase conditions, and in the presence of a catalyst comprising SSZ-42.

SSZ-42 can also be used for removing benzene from gasoline by alkylating the benzene as described above and removing the alkylated product from the gasoline.

For high catalytic activity, the SSZ-42 zeolite should be predominantly in its hydrogen ion form. Generally, the zeolite is converted to its hydrogen form by ammonium exchange followed by calcination. If the zeolite is synthesized with a high enough ratio of organo-nitrogen cation to sodium ion, calcination alone may be sufficient. It is preferred that, after calcination, at least 80% of the cation sites are occupied by hydrogen ions and/or rare earth ions.

The pure SSZ-42 zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 weight percent SSZ-42 zeolite. Usually the zeolite content will range from 10 to 90 weight percent, and more typically from 60 to 80 weight percent. The. preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene and xylene. The preferred aromatic hydrocarbon is benzene. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. The preferred olefin is propylene. These olefins may be present in admixture with the corresponding $C_2$ to $C_{20}$ paraffins, but it is preferable to remove any dienes, acetylenes, sulfur compounds or nitrogen compounds which may be present in the olefin feedstock stream, to prevent rapid catalyst deactivation. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 38° C. (100° F.) to 316° C. (600° F.), preferably 121° C. (250° F.) to 232° C. (450° F.). The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 38° C. (100° F.) to 316° C. (600° F.), but it is preferably about 121° C. (250° F.) to 232° C. (450° F.). The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

SSZ-42 can also be used as an adsorbent with high selectivities based on molecular sieve behavior and also based upon preferential hydrocarbon packing within the pores.

Xylene Isomerization

SSZ-42 may also be useful in a process for isomerizing one or more xylene isomers in a $C_8$ aromatic feed to obtain ortho-, meta- and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by distillation. The isomerate is blended with fresh feed and the combined stream is distilled to remove heavy and light by-products. The resultant $C_8$ aromatics stream is then sent to the crystallizer to repeat the cycle.

EXAMPLES

The following examples demonstrate but do not limit the present invention.

Example 1

Synthesis of N-benzyl-1,4-diazabicyclo[2.2.2]octane cation

145 Grams of 1,4-diazabicyclo[2.2.2]octane (commonly referred to as "DABCO") was dissolved in 2.5 liters of ethyl acetate and chilled to 0° C. (32° F.). 209 Grams of benzyl bromide was added dropwise while the chilled solution was stirred. Caution should be exercised because the reaction is rapid and requires cooling. The product was collected by filtration and recrystallized from a minimum of warm methanol. The recrystallized product gave a microanalysis and NMR pattern consistent with the 1:1 adduct. The quaternary ammonium compound was ion exchanged using hydroxide exchange resin AG1-X8 from BioRad. The exchanged solution was titrated for molarity and the yield of exchange was greater than 90%. The resulting compound was designated Template A.

Example 2

Synthesis of 1-azabicyclo[2.2.2]octane cation

The procedure of Example 1 was repeated using the same molar quantity of 1-azabicyclo[2.2.2]octane (commonly referred to as "quinuclidine") as the DABCO in Example 1. This compound was designated Template B.

Example 3

The procedure of Example 1 was repeated using the same molar quantity of 3-hydroxy-1-azabicyclo[2.2.2]octane in place of the DABCO. The resulting compound was designated Template C.

Example 4

Synthesis of SSZ-42

3 Millimoles of Template A as a 5.5 ml aqueous solution was used to dissolve 0.06 gram sodium borate decahydrate, and 0.6 gram Cabosil M5 silica was slurried into the resulting solution. The reaction mixture was heated in a Teflon cup of a stainless steel reactor at 150° C. (302° F.) for 17 days without agitation. A crystalline product formed which was isolated and identified as SSZ-42 by its X-ray diffraction (XRD) pattern.

Examples 5–11

Synthesis of SSZ-42

Procedures similar to that of Example 4 was used to prepare SSZ-42 using the materials and amounts shown in Table C below.

TABLE C

| Ex. No. | Template mM | Borate, gms | Water, ml | Cabosil gms | Temp. °C. (°F.) | Time (days) |
|---|---|---|---|---|---|---|
| 5 | A, 16.3 | 0.38 | 42 | 3.26 | 150 (302) | 3 |
| 6 | B, 32 | 0.80 | 80 | 6.0 | 140 (284) | 4 |
| 7 | C, 4.8 | 0.11, 1NNaOH | 13 | 0.96 | 150 (302) | 18 |
| 8 | A, 53 | 1.25 | 143 | 11.0 | 150 (302) | 4 |
| 9 | A, 2.5 | 0.17 | 10 | 0.75 | 150 (302) | 3 |
| 10 | A, 2.5 | 0.044 | 10 | 0.75 | 150 (302) | 3 |
| 11 | A, 667 | 22.67 | 1800 | 200 | 150 (302) | 5 |

In Examples 5–11, all of the reactions were seeded with SSZ-42 in the as-synthesized form to the extent of about 1% of the silica. Examples 6 and 11 were stirred at 100 RPM.

The XRD data for the as-synthesized (but not calcined) SSZ-42 prepared in Example 11 is shown in Table III below.

TABLE III

| 2Theta | d | $I/I_o$ |
|---|---|---|
| 8.219 | 10.7487 | 76.3 |
| 9.707 | 9.1041 | 6.1 |
| 13.641 | 6.4861 | 7.3 |
| 15.272 | 5.7968 | 3.2 |
| 16.033 | 5.5234 | 7.9 |
| 16.475 | 5.3762 | 13.6 |
| 19.125 | 4.6368 | 19.6 |
| 19.497 | 4.5492 | 4.2 |
| 20.597 | 4.3086 | 100.0 |
| 21.544 | 4.1213 | 21.0 |
| 21.760 | 4.0809 | 46.0 |
| 23.873 | 3.7243 | 31.8 |
| 24.337 | 3.6543 | 1.8 |
| 24.903 | 3.5725 | 10.5 |
| 25.349 | 3.5107 | 9.0 |
| 26.211 | 3.3971 | 22.3 |
| 26.751 | 3.3298 | 22.1 |
| 27.428 | 3.2491 | 2.5 |
| 27.704 | 3.2173 | 3.0 |
| 28.371 | 3.1432 | 7.7 |
| 28.934 | 3.0833 | 2.2 |
| 29.407 | 3.0348 | 15.3 |
| 30.185 | 3.9583 | 3.1 |
| 31.310 | 2.8545 | 1.6 |
| 31.784 | 2.8130 | 7.9 |
| 32.406 | 2.7605 | 3.1 |
| 33.315 | 2.6872 | 5.2 |
| 34.024 | 2.6328 | 6.1 |
| 34.721 | 2.5815 | 4.2 |
| 35.437 | 2.5310 | 3.4 |
| 35.777 | 2.5077 | 3.5 |
| 36.150 | 2.4827 | 4.3 |
| 36.477 | 2.4612 | 1.4 |
| 36.878 | 2.4353 | 6.8 |
| 40.599 | 2.2203 | 2.5 |

Example 12

Calcination of SSZ-42

The crystalline product of Example 11 was subjected to calcination as follows. The sample was heated in a muffle furnace from room temperature to 600° C. (1112° F.) in stages and under a stream of nitrogen with a very small air bleed. The stages were to 125° C. (257° F.) at 50° C. (122° F.)/hr, hold for two hours, 50° C. (122° F.)/hr to 540° C. (1004° F.), hold for four hours, 50° C. (122° F.)/hr to 600° C. (1112° F.) with a final hold for four hours. The micropore volume for nitrogen of the sample was determined to be 0.20 cc/g and a BET surface area of 470 m²/g was calculated for this material, demonstrating that SSZ-42 is a highly microporous material.

Example 13

Ion Exchange of Calcined SSZ-42

Ion exchange of calcined SSZ-42 was carried out using a 1/1/20 mass ratio of SSZ-42/ammonium acetate/water, with the mixture being heated at 95° C. (203° F.) for two hours. After cooling, the exchanged zeolite was filtered and washed with water.

The resulting product was analyzed and had the XRD data shown in Table IV below.

TABLE IV

| 2Theta | d | I/I$_o$ |
|---|---|---|
| 8.180 | 10.8001 | 100.0 |
| 9.722 | 9.0903 | 13.9 |
| 11.917 | 7.4204 | 1.5 |
| 13.162 | 6.7212 | 3.6 |
| 13.641 | 6.4862 | 4.1 |
| 13.819 | 6.4031 | 6.4 |
| 15.240 | 5.8091 | 7.3 |
| 16.042 | 5.5204 | 1.0 |
| 16.435 | 5.3893 | 1.4 |
| 16.820 | 5.2668 | 1.0 |
| 18.203 | 4.8696 | 0.9 |
| 19.179 | 4.6240 | 4.0 |
| 19.558 | 4.5352 | 1.8 |
| 20.439 | 4.3417 | 15.8 |
| 20.821 | 4.2629 | 12.0 |
| 21.459 | 4.1376 | 4.4 |
| 21.719 | 4.0886 | 12.4 |
| 23.659 | 3.7576 | 2.8 |
| 24.019 | 3.7020 | 7.8 |
| 24.412 | 3.6433 | 0.6 |
| 24.758 | 3.5932 | 2.2 |
| 24.940 | 3.5674 | 3.4 |
| 25.438 | 3.4987 | 2.6 |
| 26.400 | 3.3733 | 9.1 |
| 26.541 | 3.3557 | 10.1 |
| 27.479 | 3.2433 | 1.7 |
| 27.697 | 3.2182 | 1.0 |
| 28.300 | 3.1510 | 3.4 |
| 28.859 | 3.0912 | 0.8 |
| 29.270 | 3.0488 | 0.4 |
| 29.520 | 3.0235 | 4.1 |
| 30.081 | 2.9684 | 0.5 |
| 30.921 | 2.8896 | 1.4 |
| 31.105 | 2.8730 | 0.4 |
| 31.670 | 2.8230 | 2.5 |
| 32.179 | 2.7795 | 0.8 |
| 32.501 | 2.7527 | 1.5 |
| 33.181 | 2.6978 | 2.1 |
| 33.999 | 2.6347 | 1.5 |
| 34.945 | 2.5655 | 0.8 |
| 35.241 | 2.5447 | 0.8 |
| 35.599 | 2.5199 | 2.4 |
| 36.240 | 2.4768 | 1.9 |
| 36.759 | 2.4430 | 2.9 |

Example 14

Preparation of Aluminosilicate SSZ-42

The aluminosilicate form of SSZ-42 was made from the product of Example 12. 92 Grams of the borosilicate product of Example 12 was added to 1200 cc water and 101.2 grams of aluminum nitrate nonahydrate in the liner of a 2 liter autoclave. The reactor was sealed and heated at 140° C. (284° F.) without stirring for 3 days, and the resulting zeolite was filtered for recovery and washed with water.

The resulting product was analyzed and found to have the XRD lines shown in Table V below.

TABLE V

| 2Theta | d | I/I$_o$ |
|---|---|---|
| 8.161 | 10.8252 | 100.0 |
| 9.705 | 9.1062 | 12.1 |
| 11.851 | 7.4616 | 1.5 |
| 13.142 | 6.7314 | 3.5 |
| 13.704 | 6.4565 | 7.8 |
| 15.176 | 5.8334 | 9.2 |
| 15.991 | 5.5379 | 1.1 |
| 16.346 | 5.4184 | 1.2 |

TABLE V-continued

| 2Theta | d | I/I$_o$ |
|---|---|---|
| 19.044 | 4.6564 | 5.6 |
| 19.456 | 4.5588 | 1.6 |
| 20.355 | 4.3594 | 17.3 |
| 20.673 | 4.2931 | 14.2 |
| 21.376 | 4.1534 | 5.3 |
| 21.635 | 4.1043 | 12.4 |
| 23.827 | 3.7314 | 12.5 |
| 24.814 | 3.5852 | 4.4 |
| 25.281 | 3.5200 | 3.3 |
| 26.202 | 3.3984 | 12.3 |
| 27.285 | 3.2659 | 1.6 |
| 28.176 | 3.1646 | 3.0 |
| 28.711 | 3.1068 | 1.0 |
| 29.383 | 3.0373 | 5.4 |
| 30.725 | 2.9076 | 1.9 |
| 31.497 | 2.8381 | 3.1 |
| 32.302 | 2.7692 | 2.0 |
| 33.041 | 2.7089 | 1.9 |
| 33.796 | 2.6501 | 1.0 |
| 35.389 | 2.5344 | 3.2 |

Example 15

Constraint Index Determination 0.50 Gram of 20–40 mesh granules (after pelletization to 3000 psi and pellet breakup) of the product of Example 14 was packed into a ¼ inch stainless steel reactor tube with alundum on both sides of the zeolite bed. The reactor was placed in a Lindburg furnace and heated to 540° C. (1004° F.) for drying. At 125° C. (257° F.) helium was introduced into the reactor at 10 cc/minute and atmospheric pressure. The temperature was gradually raised to 280° C. (536° F.) over 40 minutes. Feed was introduced by means of a syringe pump at a rate of 0.62 cc/hr of a 50/50 (v/v) mixture of n-hexane and 3-methylpentane. Direct sampling onto a gas chromatograph was begun at ten minutes. This first point showed an overall conversion of 70% and a Constraint Index calculated at 0.65. Large pore behavior in cracking was observed.

Example 16

Preparation of Gallosilicate SSZ-42

5.1 Grams of the product of Example 13 was mixed with 4.85 grams of gallium nitrate nonahydrate and 82 cc of water. The resulting mixture was heated in a polypropylene bottle for 3 days at 95° C. (203° F.) and then filtered and washed to yield the gallosilicate form of SSZ-42.

The resulting product was analyzed and found to have the XRD lines shown in Table VI below.

TABLE VI

| 2Theta | d | I/I$_o$ |
|---|---|---|
| 8.142 | 10.8504 | 100.0 |
| 9.677 | 9.1325 | 13.4 |
| 11.839 | 7.4691 | 2.4 |
| 13.120 | 6.7426 | 5.1 |
| 13.720 | 6.4491 | 9.5 |
| 15.152 | 5.8426 | 11.6 |
| 15.940 | 5.5555 | 2.3 |
| 16.314 | 5.4290 | 2.6 |
| 19.024 | 4.6613 | 7.2 |
| 19.408 | 4.5699 | 2.6 |
| 20.306 | 4.3698 | 24.8 |

TABLE VI-continued

| 2Theta | d | I/I₀ |
|---|---|---|
| 20.661 | 4.2955 | 22.7 |
| 21.319 | 4.1644 | 7.7 |
| 21.567 | 4.1171 | 17.5 |
| 23.487 | 3.7847 | 2.8 |
| 23.835 | 3.7302 | 16.5 |
| 24.718 | 3.5989 | 8.2 |
| 25.214 | 3.5292 | 4.3 |
| 26.243 | 3.3931 | 18.9 |
| 27.258 | 3.2690 | 1.9 |
| 27.496 | 3.2413 | 1.4 |
| 28.101 | 3.1729 | 4.8 |
| 28.617 | 3.1168 | 2.0 |
| 29.329 | 3.0428 | 9.0 |
| 29.851 | 2.9907 | 1.3 |
| 30.711 | 2.9089 | 2.5 |
| 31.407 | 2.8460 | 5.3 |
| 32.238 | 2.7745 | 3.3 |

Example 17

Methanol Conversion to Higher Hydrocarbons

The catalyst as prepared in Examples 14 and 15 was tested for conversion of methanol. A downflow reactor, syringe pump and on-line gas chromatograph were used for the reaction. At 400° C. (752° F.) and 5 minutes on stream, the conversion of methanol is 100%, and the following hydrocarbons were analyzed in area percent:

| Hydrocarbon | Area % |
|---|---|
| Methane | 10.3 |
| Ethane/Ethylene | 24.0 |
| Propane/Propylene | 28.8 |
| Isobutane | 15.4 |
| Pentamethylbenzene | 12.6 |
| Hexamethylbenzene | 3.1 |

It can be seen that there is considerable hydrogen transfer early in the reaction for this very active and acidic zeolite. Also, the selectivities are indicative of at least one large pore system.

Example 18

Preparation of Cesium-neutralized, Platinum SSZ-42

SSZ-42 (10.00 grams, moisture-free) was mixed with 80.00 grams de-ionized water. A solution of 7.00 grams CsOH (66,450 ppm Cs) in 23 grams de-ionized water was then added to the catalyst slurry and shaken for 24 hours. The pH after exchange was 9.8. The catalyst was filtered and air dried for 72 hours. It was then dried at 121° C. (250° F.) for 16 hours and then calcined in air at 299° C. (570° F.) for 2 hours.

The calcined Cs-SSZ-42 was mixed with 80.00 grams de-ionized water and 30.00 grams of a solution of platinumtetraamine dichloride in de-ionized water was added to the mixture. The resulting catalyst slurry was shaken for 18 hours. It was then filtered and air dried to constant moisture. The air dried catalyst was further dried at 121° C. (250° F.) for 16 hours and then calcined in air at 299° C. (570° F.) for 2 hours. The finished catalyst had 4 wt % Cs and 0.5 wt % Pt. The cyclohexane micropore volume of the finished catalyst was 0.133 cc/grams and the Pt dispersion calculated from hydrogen adsorption was 72%.

Example 19

Reforming to Benzene Using SSZ-42 Catalyst

The cesium neutralized, platinum SSZ-42 catalyst of Example 18 (0.45 gram) was tested in a small pilot plant at 130 psig, 3.0 weight hourly space velocity, 3.0 hydrogen to hydrocarbon molar ratio and once-through hydrogen. The hydrocarbon feed was 149° C. (300° F.) end point naphtha of the following composition:

67 wt % paraffins 24 wt % naphthenes 9 wt % aromatics

Catalyst temperature was adjusted to maintain a 95 research octane target. The performance of this catalyst was compared to a commercial reforming catalyst and the results are shown in Table D below.

TABLE D

| | Commercial Catalyst | Pt/Cs-Beta Zeolite | Pt/Cs-SSZ-42 | Pt/Cs-SSZ-42 |
|---|---|---|---|---|
| SOR Activity, °C. (°F.) | 494 (922) | 523 (973) | 498 (928) | 494 (921) |
| Pressure, PSIG | 130 | 130 | 130 | 60 |
| Octane (Calc. RON) | 95.0 | 95.0 | 95.0 | 95.1 |
| $C_{5+}$ Yield, wt % | 84.0 | 83.5 | 75.9 | 82.1 |
| Aromatics Yield (wt %)[a] | | | | |
| Benzene | 3.5 | 4.8 | 10.6 | 9.6 |
| Toluene | 24.8 | 26.4 | 24.6 | 27.2 |
| $C_8$ Aromatics | 19.0 | 16.7 | 9.6 | 11.8 |
| $C_9$ Aromatics | 3.7 | 2.8 | 1.0 | 1.4 |

[a]Based on feed.

The results in Table P show that SSZ-42 catalyst can be prepared with high activity and high aromatics selectivity while being used at low operating pressure.

The remarkable stability of the SSZ-42 catalyst is shown in the drawing. There, run hours versus temperature are plotted for a reaction similar to that described in Example 19. The reactions were carried out at 3.0 WHSV, 3.0 $H_2$:hydrocarbon and using a light naptha feed (149° C. (300° F.) end point). The plots shown in the drawing are as follows:

| Plot | Catalyst | Conditions | Fouling Rate |
|---|---|---|---|
| A | Pt/Cs-SSZ-42 | 80 psig | 0.006° F./hr |
| B | Commercial | 130 psig | 0.08° F./hr |
| B' | Commercial | 80 psig | 0.23° F./hr |
| C | Pt/Cs-beta zeolite | 130 psig | 0.01° F./hr |
| C' | Pt/Cs-beta zeolite | 80 psig | 0.16° F./hr |

Example 20

Preparations of SSZ-42

SSZ-42 was prepared as described in Example 4, except that one-half of the sodium borate was replaced with sodium aluminate trihydrate. After 6 days at 150° C. (302° F.), the recovered product was SSZ-42. The lattice constants for the diffraction lines indicated a shift to a larger unit cell, consistent with aluminum incorporation into the product (as is also seen in Example 14).

Example 21

Preparation of FCC Catalyst

A modified form of FCC catalyst can be prepared from SSZ-42 and used in MAT testing. 4 Grams of Catapal alumina (solids basis) was peptized with 0.8 grams formic acid in 40 ml water. 22 Grams of kaolin (solids basis) was mixed in and processed in a blender. 10 Grams of Al-SSZ-42, from Example 14 was mixed in 20 ml water and this mixture was subsequently also blended in. After blending, this catalyst mixture was dried at 120° C. (248° F.) overnight. Next the solids were meshed to 100–325 and then calcined by placing in an oven already at 600° C. (1112° F.) (3 hours of calcination). A comparable comparative catalyst was made from Y zeolite (using CBV 500 from PQ Corporation). A blank was made by making one more catalyst where kaolin replaced the amount of zeolite used in the preparation.

Example 22

Testing of SSZ-42 (Fresh) in FCC Application

MAT testing was carried out with a 3.2 Catalyst/Oil ratio, a 75 second contact time and at 530° C. (986° F.) using a FCC feed. The data for the three prepared materials from Example 21 is given in Table E below.

TABLE E

|  | Kaolin blank | Y zeolite cat. | SSZ-42 cat. |
| --- | --- | --- | --- |
| Wt % Conv. 220° C. (428° F.) minus | 23 | 74 | 55 |
| Coke | 2.9 | 17 | 5.2 |
| Hydrogen | 0.3 | 0.3 | 0.3 |
| Methane | 0.5 | 1.5 | 0.5 |
| Ethane | 0.4 | 1.3 | 0.4 |
| Ethylene | 0.3 | 0.9 | 1.5 |
| Propane | 0.3 | 8.8 | 4.4 |
| Propylene | 0.7 | 1.6 | 4.3 |
| Isobutane | 0.1 | 6.6 | 7.8 |
| n-Butane | 0.1 | 3.6 | 2.4 |
| Isobutene | 0.4 | 0.3 | 1.8 |
| Total butenes | 0.8 | 1.5 | 4.0 |
| Pentenes | 0.4 | 0.8 | 1.7 |
| Gasoline | 16.8 | 31.1 | 24.7 |

It can be seen that the fresh SSZ-42 composited catalyst shows useful conversion of FCC feed, and in particular, makes a high slate of useful gas products (such as isobutane and olefins) as well as gasoline.

What is claimed is:

1. A process for converting hydrocarbons comprising contacting a hydrocarbonaceous feed at hydrocarbon converting conditions with a catalyst comprising a zeolite having a mole ratio of an oxide selected from silicon oxide, germanium oxide and mixtures thereof to an oxide selected from aluminum oxide, gallium oxide, iron oxide, titanium oxide, boron oxide and mixtures thereof greater than about 10 and having the X-ray diffraction lines of Table I.

2. A process according to claim 1 which is a hydrocracking process comprising contacting a hydrocarbon feedstock under hydrocracking conditions with the catalyst.

3. A process according to claim 1 which is a dewaxing process comprising contacting a hydrocarbon feedstock under dewaxing conditions with the catalyst.

4. A process according to claim 1 which is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 300° C., under aromatic conversion conditions with the catalyst.

5. The process of claim 4 wherein the catalyst contains a Group VIII metal component.

6. A process according to claim 1 which is a process for converting heavy paraffinic and naphthenic feedstocks boiling between about 200° C. and about 300° C. to lighter aromatics under aromatic conversion conditions with the catalyst.

7. The process of claim 6 wherein the catalyst contains a Group VIII metal component.

8. A process according to claim 1 which is a catalytic cracking process comprising contacting a hydrocarbon feedstock in a reaction zone under catalytic cracking conditions in the absence of added hydrogen with the catalyst.

9. The process of claim 8 wherein the catalyst additionally comprises a large pore crystalline cracking component.

10. The process of claim 9 wherein the catalyst composition comprises a physical mixture of the two components.

11. The process of claim 10 wherein the two catalyst components are incorporated in an inorganic matrix.

12. A process according to claim 1 which is an isomerizing process for isomerizing $C_4$ to $C_7$ hydrocarbons, comprising contacting the catalyst and at least one Group VIII metal with a feed having normal and slightly branched $C_4$ to $C_7$ hydrocarbons under isomerizing conditions.

13. The process of claim 12 wherein the catalyst has been calcined in a steam/air mixture at an elevated temperature after impregnation of the Group VIII metal.

14. The process of claim 13 wherein the Group VIII metal is platinum.

15. A process according to claim 1 which is a process for alkylating an aromatic hydrocarbon which comprises contacting under alkylation conditions at least a mole excess of an aromatic hydrocarbon with a $C_2$ to $C_{20}$ olefin under at least partial liquid phase conditions and in the presence of the catalyst.

16. The process of claim 15 wherein the olefin is a $C_2$ to $C_4$ olefin.

17. The process of claim 15 wherein the aromatic hydrocarbon and olefin are present in a molar ratio of about 4:1 to about 20:1, respectively.

18. The process of claim 17 wherein the aromatic hydrocarbon is selected from the group consisting of benzene, toluene, xylene, or mixtures thereof.

19. A process according to claim 1 which is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

20. The process of claim 19 wherein the aromatic hydrocarbon and the polyalkyl aromatic hydrocarbon are present in a molar ratio of from about 1:1 to about 25:1, respectively.

21. The process of claim 19 wherein the aromatic hydrocarbon is a member selected from the group consisting of benzene, toluene, xylene, or mixtures thereof.

22. The process of claim 19 wherein the polyalkyl aromatic hydrocarbon is a dialkylbenzene.

23. A process according to claim 1 which is a process to convert paraffins to aromatics which comprises contacting paraffins with the catalyst, said catalyst further comprising gallium, zinc, or a compound of gallium or zinc.

24. A process according to claim 1 which is a process for isomerizing olefins comprising contacting said olefin with the catalyst under conditions which cause isomerization of said olefin.

25. A process according to claim 1 which is a process for isomerizing an isomerization feed containing an aromatic $C_8$ stream of ethylbenzene or xylene isomers or mixtures thereof, wherein a more nearly equilibrium ratio of ortho-, meta- and para-xylenes is obtained, said process comprising contacting said feed under isomerization conditions with the catalyst.

26. A process for converting lower alcohols and other oxygenated hydrocarbons comprising contacting said lower alcohol or other oxygenated hydrocarbon with a catalyst a zeolite having a mole ratio of an oxide selected from silicon oxide, germanium oxide and mixtures thereof to an oxide selected from aluminum oxide, gallium oxide, iron oxide, titanium oxide, boron oxide and mixtures thereof greater than about 10 and having the X-ray diffraction lines of Table I under conditions to produce liquid products.

* * * * *